United States Patent [19]

Bally et al.

[11] Patent Number: 5,595,756
[45] Date of Patent: Jan. 21, 1997

[54] LIPOSOMAL COMPOSITIONS FOR ENHANCED RETENTION OF BIOACTIVE AGENTS

[75] Inventors: Marcel B. Bally, Bowen Island; Nancy L. Boman, Richmond; Pieter R. Cullis, Vancouver; Lawrence D. Mayer, North Vancouver, all of Canada

[73] Assignees: Inex Pharmaceuticals Corporation; University of British of Columbia, both of Vancouver, Canada

[21] Appl. No.: 172,140

[22] Filed: Dec. 22, 1993

[51] Int. Cl.$^6$ ............................................. A61K 9/127
[52] U.S. Cl. ........................... 424/450; 264/4.1; 264/4.3
[58] Field of Search ..................... 424/450; 428/402.2; 264/4.1, 4.3

[56] References Cited

U.S. PATENT DOCUMENTS

| | | | |
|---|---|---|---|
| 4,619,935 | 8/1986 | Robison | 514/281 |
| 4,952,408 | 8/1990 | Rahman | 424/450 |
| 5,225,212 | 7/1993 | Martin | 424/450 |

FOREIGN PATENT DOCUMENTS 0274219  7/1988  European Pat. Off. .

OTHER PUBLICATIONS

Allen, T. M., et al. (1987) "Large unilamellar liposomes with low uptake into the reticuloendothelial system," *FEBS Lett*, 223(1):42–46.
Allen, T. M., et al. (1989) "Liposomes with prolonged circulation times: factors affecting uptake by reticuloendothelial and other tissues," *Biochim Biophys Acta*, 981:27–35.
Allen. T. M., et al. (1991) "Liposomes containing synthetic lipid derivative of poly(ethlyene glycol) show prolonged circulation half–lives in vivo," *Biochim Biophys Acta*, 1066:29–36.
Allen, T. M., et al. (1991) "Uptake of liposomes by cultured mouse bone marrow macrophages: influence of liposome composition and size," *Biochim Biophys Acta*, 1061:56–63.
Allen, T. M., et al. (1992) "Stealth Liposomes: an improved sutstained release system of 1–B–D–arabinofuranosylcytosine," *Cancer Res*, 52:2431–2439.
Bally, M. B., et al. (1990) "Liposomes with entrapped doxorubicin exhibit extended blood residence times," *Biochim. Biophys. Acta*, 1023:133–139.
Boman, N. L., et al. (1993) "Optimization of the retention properties of vincristine in liposomal systems," *Biochim Biophys Acta* 1152:253–258.
Boman, N. L., et al. 1994 "Liposomal vincristine which exhibits increased drug retention and increased circulation longevity cures mice bearing P388 tumors," *Cancer Res.*, 54:2830-2833.
Carter, S. K., et al. (1976) "Plant products in cancer chemotherapy," *Cancer Treat Rep.* 60(8):1141–1155.
Chakrabarti, A. C., et al. (1992) "Uptake of basic amino acids and peptides into liposomes in response to transmembrane pH gradients," *Biophys. J.*, 61:228–234.
Chonn, A., et al. (1992) "Association of blood proteins with large unilamellar liposomes in vivo: relation to circulation lifetimes," *J. Biol Chem*, 267(26):18759–18765.
Derksen, J. T. P., et al. (1987) "Processing of different liposome markers after *in vitro* uptake of immunoglobulin--coated liposomes by rat liver macrophages," *Biochim. Biophys. Acta*, 931:33–40.
Fichtner, I, et al. (1981) "Therapeutic evaluation of liposome–encapsulated daunoblastin in murine tumor models," *Neoplasma (Bratisl.)*, 28:141–149.

(List continued on next page.)

Primary Examiner—Gollamudi S. Kishore
Attorney, Agent, or Firm—Townsend and Townsend and Crew

[57] ABSTRACT

Liposomal compositions encapsulating bioactive agents and having improved circulation longevity of the agents are disclosed. Such liposomes combine a low pH of the solution in which a bioactive agent is entrapped and a sugar-modified lipid or an amine-bearing lipid, the combination of which enhances the retention of the encapsulated bioactive agent and thereby promotes circulation longevity. The present invention also discloses methods of making and using such compositions.

10 Claims, 6 Drawing Sheets

OTHER PUBLICATIONS

Forssen, E. A., et al. (1981) "Use of anionic liposomes for the reduction of chronic doxorubicin–induced cardiotoxicity," *Proc. Natl. Acad. Sci USA* 78:1873–1877.

Gabizon, A., et al. (1982) "Enhancement of adriamycin delivery to liver metastatic cells with increased tumoricidal effect using liposomes as drug carriers," *Cancer Res.* 43:4730–4735.

Gabizon, A., et al. (1982) "Liposomes as *in vivo* carriers of adriamycin: reduced cardiac uptake and preserved antitumor activity in mice," *Cancer Res.* 42:4734–4739.

Gabizon, A., et al. (1988) "Liposome formulations with prolonged circulation time in blood and enhanced uptake by tumors," *Proc. Natl. Acad. Sci USA*, 85:6949–6953.

Gregoriadis, G., et al. (1975) "Treatment of tumour bearing mice with liposome–entrapped actinomycin D prolongs their survival," *Res. Commun. Chem. Pathol Pharmacol.*, 10(2):351–362.

Herman, E. H., et al. (1983) "Prevention of chronic doxorubicin cardiotoxicity in beagles by liposomal encapsulation," *Cancer Res.*, 43:5427–5432.

Hunt, C. A., et al. (1979) "Retention of cytosine arabinoside in mouse lung following intravenous administration in liposomes of different size," *Drug Metab. Dispos.*, 7:124–128.

Jackson, D. V. Jr., et al. (1979) "Cytotoxic thresholds of vincristine in a murine and a human leukemia cell line *in vitro*," *Cancer Res.*, 39:4346–4349.

Jackson, D. V., et al. (1986) "Moderate–dose vincristine infusion in refractory breast cancer," *Am. J. of Clin Onc.*, 9(5):376–378.

Jackson, D. V. Jr., et al. (1986) "Vincristine infusion in refractory gynecologic malignancies," *Gynecol. Onc.*, 25(2):212–216.

Klibanov, A. L., et al. (1990) "Amphipathic polyethyleneglycols effectively prolong the circulation time of liposomes," *FEBS Lett*, 268(1):235–237.

Klibanov, A. L., et al. (1991) "Activity of amphipathic poly(ethylene glycol) 5000 to prolong the circulation time of lipsomes depends on the liposome size and is unfavorable for immunoliposome binding to target," *Biochim Biophys Acta* 1062:142–148.

Kobayashi, T., et al. (1977) "Enhancement of anti–tumor activity of 1–β–D–arabinofuranosylcytosine by encapsulation of liposomes," *Int. J. Cancer,* 20:581–587.

Liu, D., et al. (1990) "pH–sensitive, plasma–stable liposomes with relatively prolonged residence in circulation," *Biochim Biophys Acta* 1022:348–354.

Mayer, L. D., et al. (1989) "Influence of vesicle size, lipid composition, and drug–to–lipid ratio on the biological activity of liposomal doxorubicin in mice," *Canc. Res.*, 49:5922–5930.

Mayer, L. D., et al. (1990) "Strategies for optimizing liposomal doxorubicin," *J. of Liposome Res.*, 1(4):463–480.

Mayer, L. D., et al. (1990) "Liposomal vincristine preparations which exhibit decreased drug toxicity and increased activity against murine L1210 and P388 tumors," *Cancer Res.* 50:575–579.

Mayer, L. D., et al. (1990) "Comparison of free and liposome encapsulated doxorubicin tumor drug uptake and antitumor efficacy in the SC115 murine mammary tumor," *Cancer Lett.,* 53:183–190.

Mayer, L. D., et al. (1990) "Characterization of liposomal systems containing doxorubicin entapped in response to pH gradients," *Biochim Biophys. Acta,* 1025:143–151.

Mayer, L. D., et al. (1993) "Identification of vesicle properties that enhance the antitumour activity of liposomal vincristine against murine L1210 leukemia," *Cancer Chemother Pharmacol,* 33:17–24.

Mayhew, E., et al. (1985) "The use of liposomes as carriers of therapeutic agents," *Prog. Clin. Biol. Res.* 172B:301–310.

Mui, B. L. S., et al. (1993) "Osmotic properties of large unilamerllar vesicles prepared by extrusion," *Biophys. J.,* 64:443–453.

Olson, F., et al. (1979) "Preparation of liposomes of defined size distribution by extrusion through polycarbonate membranes," *Biochim. Biophys. Acta,* 557:9–23.

Owellen, R. J., et al. (1976) "Inhibition of tubulin–microtubule polymerization by drugs of the vinca alkaloid class," *Cancer Res.*, 36:1499–1502.

Owellen, R. J., et al. (1972) "The binding of vincristine, vinblastine, and colchicine to tubulin," *Biochem Biophys Res. Commun.* 47(4):685–691.

Rahman, A., et al. (1982) "Doxorubicin–induced chronic cardiotoxicity and its protection by liposomal administration," *Cancer Res.*, 42:1817–1825.

Senior, J., et al. (1991) "Influence of surface hydrophilicity of liposomes on their interaction with plasma protein and clearance from the circulation: studies with poly(ethylene glycol)–coated vesicles," *Biochim Biophys Acta,* 1062:77–82.

Sieber, S. M., et al. (1976) "Pharmacology of antitumor agents from higher plants," *Cancer Treat Rep.*, 60:1127–1139.

Woo, S. Y., et al. (1983) "Liposomal methotrexate in the treatment of murine L1210 leukemia," *Cancer Drug Delivery,* 1(1): 59–62.

Chonn, A., et al. (1992) "Ganglioside $G_{m1}$ and hydrophilic polymers increase liposome circulation times by inhibiting the association of blood proteins," *J. of Liposome Research,* 2(3):397–410.

Parr, M. J., et al. (1993) "The presence of $G_{m1}$ in liposomes with entrapped doxorubicin does not prevent RES blockade," *Biochimica et Biophysica Acta,* 1168:249–252.

*rac*-1,2-DIOLEOYL-3-*N,N*-DIMETHYLAMINOPROPANE

AL2

*rac*-1-OLEOYL-2-HYDROXY-3-*N,N*-DIMETHYLAMINOPROPANE

| AL3 | R = $CH_3$ | 2-ACETYL |
| AL4 | R = $(CH_2)_2 CH_3$ | 2-BUTYRYL |
| AL5 | R = $(CH_2)_8 CH_3$ | 2-DECANOYL |

AL6

*rac*-1,2-DIDECANOYL-3-*N,N*-DIMETHYLAMINOPROPANE

*FIG. 6.*

LIPOSOMAL COMPOSITIONS FOR ENHANCED RETENTION OF BIOACTIVE AGENTS

TECHNICAL FIELD

The present invention is generally directed toward liposomes having improved retention of bioactive agents, and to methods for making and using these compositions. This invention is more particularly related to the enhanced retention of bioactive agents by liposomes which include a sugar-modified lipid or an amine-bearing lipid and which encapsulate a solution with a low pH.

BACKGROUND OF THE INVENTION

Despite enormous investments of financial and human resources, no cure exists for a variety of diseases. For example, cancer remains one of the major causes of death. A number of bioactive agents have been found, to varying degrees, to be effective against tumor cells. However, the clinical use of such antitumor agents has been highly compromised because of treatment-limiting toxicities.

In order to decrease drug-induced toxic side effects, antitumor agents have been encapsulated in liposomes. Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (non-polar) "tails" of the lipid monolayers orient toward the center of the bilayer while the hydrophilic (polar) "heads" orient toward the aqueous phase. The current state of the art is such that liposomes may be reproducibly prepared using a number of techniques.

Liposome encapsulation of various antitumor agents has been shown to decrease drug-induced toxic side effects while maintaining or, in some instances, increasing antitumor activity. Reduction of toxicity results from the ability of liposomes to decrease drug exposure, and subsequent damage, to susceptible tissues. The mechanism of the antitumor activity of entrapped drugs is less well understood, but may result from the capacity of liposomes to slowly release encapsulated drug into the circulation or alternatively passive targeting of liposomes and their contents to tumor sites. A problem, however, with the encapsulation of antitumor agents is that many of these drugs have been found to be rapidly released from liposomes after encapsulation.

An example of an antitumor agent is vincristine, which is a member of the Vinca alkaloid class and is derived from the periwinkle plant. It is an important anticancer drug in that it displays effectiveness against a wide variety of neoplasms including both the Hodgkin's and non-Hodgkin's lymphomas, acute lymphoblastic leukemia, embryonal rhabdomyosarcoma, neuroblastoma, breast carcinoma, and Wilm's tumor. It is a cell-cycle specific drug which arrests cell growth exclusively during metaphase by attaching to the growing end of microtubules and terminating their assembly. For this reason, it is advantageous to expose neoplastic cells to the drug for prolonged periods of time. This effect has been demonstrated in vitro by Jackson and Bender (*Cancer Res.* 39:4346, 1979), and has been confirmed using the murine L1210 leukemic cell line (Mayer et al., *Cancer Chemother. Pharmacol.* 33:17–24, 1993). The importance of this relationship in the treatment of human malignancies is supported by clinical trials where patients refractory to bolus vincristine therapy exhibited increased response rates when the drug was administered as a 5-day infusion.

Liposomal formulations of vincristine have been shown to exhibit reduced toxicity and enhanced efficacy compared to free drug. The antitumor activity of vincristine appeared to be dependent on the circulation lifetime of the encapsulated drug. Circulation longevity (of liposomally entrapped bioactive agent) in turn is dependent, in part, on the rate of agent release from liposomes in the blood. Therefore, enhancement of the retention of a bioactive agent in liposomes is desirable as it will increase the circulation lifetime of the encapsulated agent, thereby improving its therapeutic activity.

Thus, there is a need in the art for liposomal bioactive agent preparations with improved circulation longevity. The present invention fulfills this need, and further provides other related advantages.

SUMMARY OF THE INVENTION

Briefly stated, the present invention provides a variety of liposomal bioactive agent compositions, and methods of making and using such compositions. In one aspect, the present invention provides compositions comprising liposomes having encapsulated therein both a bioactive agent and a buffered solution having a pH of 2 to 3, the liposomes containing a sugar-modified lipid or an amine-bearing lipid. In one embodiment, the composition encapsulates a solution with a pH of 2. In another embodiment, the lipid is selected from the group consisting of $G_{M1}$, stearylamine, sphingosine, and the amino lipids according to FIG. 6. In another embodiment, the bioactive agent is an anticancer agent.

In another aspect, the present invention provides a method for the production of liposomes encapsulating a bioactive agent, comprising the steps of:

(a) hydrating a lipid film in a buffered first solution having a pH of 2 to 3 to yield liposomes, the lipid film containing a sugar-modified lipid or an amine-bearing lipid;

(b) contacting the liposomes with a second solution, said second solution containing a bioactive agent;

(c) increasing the pH of the mixture from step (b) to a pH not above the $pK_a$ of the bioactive agent; and (d) incubating the mixture under conditions and for a time sufficient to promote entrapping of the bioactive agent by the liposome, thereby producing liposomes that encapsulate a bioactive agent and that contain a sugar-modified lipid or an amine-bearing lipid.

In one embodiment, the first solution has a pH of 2. In another embodiment, the lipid is selected from the group consisting of $G_{M1}$, stearylamine, sphingosine, and the amino lipids according to FIG. 6. In another embodiment, the bioactive agent is an anticancer agent.

In another aspect, the liposomal bioactive agent compositions of the present invention are combined with a pharmaceutically acceptable carrier or diluent.

In yet another aspect of the present invention, methods are provided for treating diseases in a warm-blooded animal. In one embodiment, the method comprises administering a therapeutically effective amount of an above-described composition for treating cancer. In another embodiment, the method comprises treating cancer by administering a therapeutically effective amount of a composition produced by the above-described method.

DESCRIPTION OF THE INVENTION

As noted above, the present invention provides liposomal bioactive agent compositions, and methods of making and using such compositions. An advantage of the compositions of the present invention is that the retention of a bioactive agent in the liposome is enhanced and, thereby, the circulation lifetime of the bioactive agent is increased. In addition, the therapeutic activity of such compositions is significantly improved.

The compositions of the present invention comprise liposomes which encapsulate a bioactive agent in a solution having a low pH and which contain a sugar-modified lipid or an amine-bearing lipid. The disclosure of the present invention shows, unexpectedly, that lowering the pH of the solution in which a bioactive agent is entrapped within a liposome and including in the liposomal membrane a sugar-modified lipid or an amine-bearing lipid synergistically combine to significantly increase the bioactive agent concentration in the plasma.

Compositions of the present invention may be formed in a variety of ways, including by active or passive loading methodologies. For example, bioactive agents may be encapsulated using a transmembrane pH gradient loading technique. General methods for loading liposomes with bioactive agents through the use of a transmembrane potential across the bilayers of the liposomes are well known to those in the art (e.g., U.S. Pat. Nos. 5,171,578 and 5,077,056). However, as disclosed within the present invention, in the embodiment where a transmembrane pH gradient is imposed across the liposome membrane, the methodology is modified for lower internal liposomal pH.

In brief, for example, lipids are first dissolved in an organic solvent, such as ethanol, and gently heated (e.g., 60° C. for 30 minutes). The lipid components used in forming the liposomes may be selected from a variety of vesicle-forming lipids, typically including phospholipids and sterols (e.g., U.S. Pat. Nos. 5,059,421 and 5,100,662). Representative examples of lipids suitable for the preparation of liposomes include cholesterol, distearoylphosphatidylcholine, phosphatidylglycerol, phosphatidylethanolamine, phosphatidylcholine, partially hydrogenated phosphatidylcholine, dipalmitoylphosphatidyl glycerol, dipalmityolphosphatidylcholine, dioleylphosphatidylcholine, and mixtures thereof. In addition, one or more lipids that contribute to the retention of entrapped bioactive agents are included. Such lipids include sugar-modified lipids and amine-bearing lipids. Representative examples of sugar-modified lipids include gangliosides, such as $G_{M1}$, $G_{M2}$ or $G_{M3}$, and derivatives thereof. Representative examples of amine-bearing lipids include stearylamine, sphingosine, the amino lipids according to FIG. 6, and derivatives thereof.

To the dissolved lipids, a pre-heated aqueous solution with a pH of less than 4 is then added while vigorously mixing. For example, a 60° C. solution containing 300 mM buffer is added, in a ratio of 3 mL solution per 100 mg lipid, while vigorously vortexing. Preferred buffers include citrate, maleate and glutamate. Citrate is particularly preferred. The pH of the solution added to the lipids is less than 4, with a pH of about 2 to 3 preferred. A pH of about 2 is particularly preferred. Following mixing, the resulting multilamellar vesicles ("MLVs") may be heated (e.g., 60° C. for an additional 30 min.) and extruded through an extrusion device to convert the MLVs to unilamellar liposome vesicles. The organic solvent used initially to dissolve the lipids may be removed from the liposome preparation by dialysis. The dialysis solution is a low pH solution identical to that previously added to the dissolved lipids. The resulting liposomes are substantially free of organic solvent and have an interior pH of less than 4 (the exact pH dependent upon the pH of the solution initially added to the dissolved lipids).

One or more bioactive agents may be entrappeal in the low pH liposomes using transmembrane pH gradient loading. By raising the pH of the solution external to the liposomes, a pH differential will exist across the liposome bilayer. Thus, a transmembrane potential is created across the liposome bilayer and a bioactive agent is loaded into the liposomes by means of the transmembrane potential. In brief, for example, low pH liposome vesicles and a bioactive agent are mixed (e.g., to achieve an agent-to-lipid ratio of about 0.1:1). The pH of the mixture (i.e., the pH external to the liposomes) is generally raised to a pH approaching the $pK_a$ of the agent (typically to neutrality or basic pH for many agents) and then heated (e.g., 60° C. for 10 min.) under conditions and for a time sufficient to permit uptake of the bioactive agent into the liposomes. For bioactive agents with amine groups capable of being protonated, the pH is typically raised to about pH 7–9. For example, for vincristine the pH is raised to pH 7.0–7.2 (e.g., using 0.5M $Na_2HPO_4$). Alternatively, an agent may be loaded passively into the low pH liposomes. Entrapment of a bioactive agent may be determined using spectroscopic assays or liquid scintillation counting (where radiolabeled), following separation of liposomes from free (non-entrapped) bioactive agent (e.g., by chromatography).

A wide variety of bioactive agents can be entrapped within the liposomes according to the present invention. Such bioactive agents include positively charged anticancer (antineoplastic) agents, anti-malarial agents, calcium channel blockers, local anesthetics, adrenergic antagonists, antiarrhythmics, cholinergic agents, biogenic amines, antidepressants, antihistamines, antiprotozoan agents, analgesics, and multiple drug resistance ("MDR") inhibitors. Preferred anticancer agents include vincristine, daunombicin, mitoxantrone, epimbicin, doxorubicin, vinblastine and tamoxifen. Preferred anti-malarial agents include quinidine and chloroquine. A preferred calcium channel blocker is verapamil. Preferred local anesthetics include lidocaine, chlorpromazine, prochlorperazine, trifluoperazine and dibucaine. Preferred adrenergic antagonists include propranolol and timolol. A preferred antiarrhythmic is quinidine. Preferred cholinergic agents include pilocarpine, physostigmine and nicardapine. Preferred biogenic amines include dopamine and serotonin. A preferred antidepressant is imipramine. A preferred antihistamine is diphenhydramine. .A preferred antiprotozoan agent is quinacrine. A preferred analgesic is codeine. Preferred MDR inhibitors include prochlorperazine, trifluoperazine, flupenthixol, tomoxifen and vindoline. It will be evident to those of ordinary skill in the art that, although certain agents are described as illustrative, numerous other agents are also suitable within the liposome compositions of the present invention.

Circulation longevity of liposomal bioactive agent compositions may be assessed by plasma clearance studies. In brief, for example, liposomes with or without loaded agent are injected into a tail vein of a mouse. Typically, the liposomes will contain radioactively labeled lipid (e.g., $^{14}$C-cholesteryl hexadecylether), with or without radioactively labeled bioactive agent. At various time points, blood is collected from anaesthetized mice via cardiac puncture. The blood cells are separated and the plasma assayed for liposomal lipid and/or bioactive agent (e.g., using scintillation counting for radiolabeled lipid or bioactive agent). The disclosure of the present invention shows that incorporation into liposomes of a sugar-modified lipid or an amine-bearing lipid in combination with the use of an entrapped solution with a low pH results in an unexpected improvement in bioactive agent circulation lifetimes.

Figure 1A:
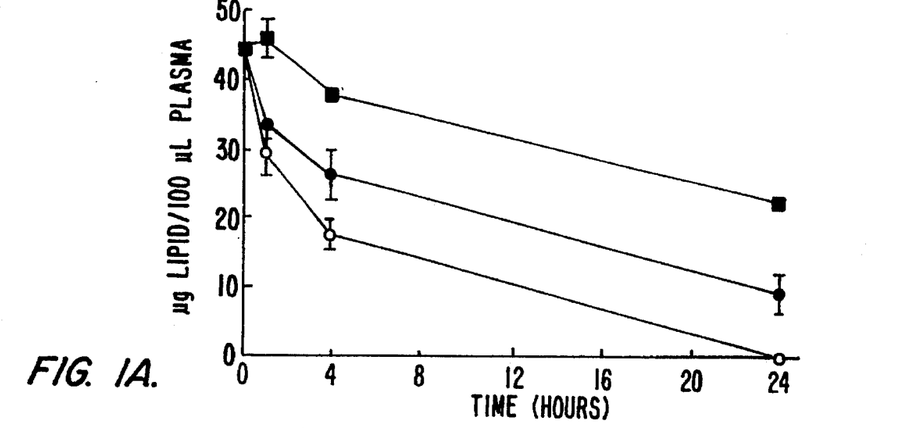
FIGS. 1A–C graphically illustrate the influence of $G_{M1}$ incorporation and entrapped vincristine on the plasma clearance (panel A), liver uptake (panel B), and spleen uptake (panel C) of 100 nm DSPC/Chol liposomes. Liposomes were all administered i.v. at a lipid dose of 20 mg/kg. Vincristine was encapsulated at a drug-to-lipid ratio of 0.1:1 (wt:wt) using the transmembrane pH gradient loading technique with liposomes prepared in 300 mM citrate butler pH 4. $G_{M1}$ was incorporated at a level of 10 mol % in DSPC/Chol liposomes (45 mol % cholesterol). Liposomal lipid was measured using the non-exchange, non-metabolizable lipid marker $^{14}C$-cholesteryl hexadecyl ether. Lipid levels were determined for drug free DSPC/Chol liposomes (O), DSPC/Chol liposomal vincristine (●), and $G_{M1}$/DSPC/Chol liposomal vincristine (■). Error bars represent standard deviations from at least four mice.
Figure 1B:
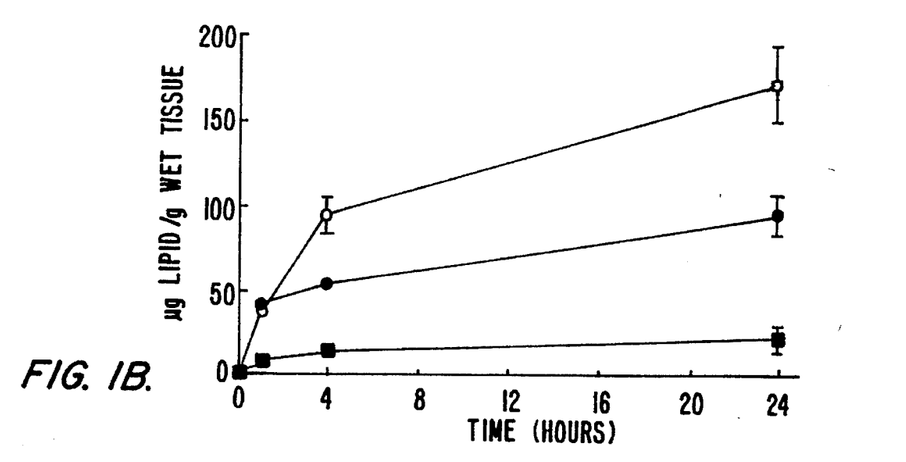
Figure 1C:
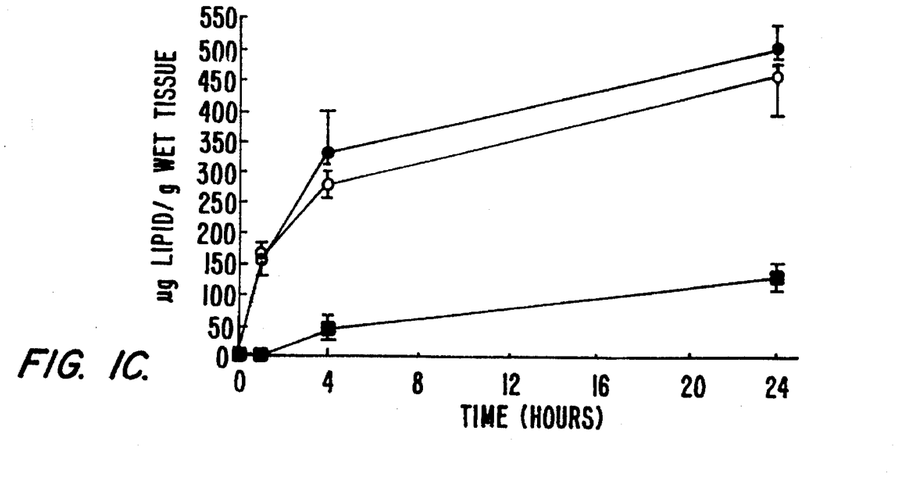

In a similar manner, biodistribution studies may be performed on selected tissue/organs from injected mice by detecting liposomal lipid and/or bioactive agent in digested, tissue homogenate samples. The addition to liposomes of a sugar-modified lipid or amine-bearing lipid (e.g., $G_{M1}$ as shown in FIG. 1) reduces significantly the liposomal lipid accumulation in liver and spleen.

The effects of a liposomal bioactive agent composition of the present invention may be examined in vitro or in vivo. For in vitro antitumor studies, for example, a liposomal anticancer agent composition can be contacted with a tumor cell line. In brief, such a composition is incubated with cultured tumor cells and the viability of the cells is measured to demonstrate the cytotoxicity of the encapsulated anticancer agent. For in vivo studies, an animal model system may be utilized. For example, for in vivo antitumor studies, the P388 lymphocytic leukemia model can be used. In brief, mice are injected i.p. with P388 cells. Liposomal anticancer agent compositions or saline only are administered (i.v.) 24 hours after tumor inoculation. .Animal weights and mortality are monitored daily. As disclosed herein, the liposomal anticancer agent compositions of the present invention (i.e., compositions which combine a reduced internal pH of the liposomes and incorporation of a sugar-modified lipid or amine-bearing lipid) exhibit significantly greater efficacy in the P388 tumor model. For example, in the encapsulated vincristine embodiment which combines a liposome internal pH of 2 with the presence of $G_{M1}$ in the liposome bilayer, administration of the composition at 2, 3 or 4 mg/kg to P388-inoculated mice consistently produced long term survivors.

Liposome compositions of the present invention may be administered to other warm-blooded animals, such as humans. Depending upon the particular bioactive agent or combination of agents encapsulated, such compositions may be used to treat diseases or induce conditions in warm-blooded animals. Examples of uses of the compositions of the present invention are for treating cancer, for treating malaria, treating a disease for which a calcium channel blocker is effective (e.g., supraventricular tachyarrhythmia), inducing local anesthesia, treating a disease for which an adrenergic antagonist is effective (e.g., hypertension and cardiac arrhymias), treating arrhythmia, treating a disease for which a cholinergic agent is effective (e.g., glaucoma), treating a disease for which a biogenic amine is effective (e.g., treatment of shock), treating depression, treating allergies, treating a disease involving a protozoan (e.g., giardia), inducing analgesia, or treating a disease for which a MDR inhibitor is effective (e.g., tumors resistant to chemotherapy). For administration to humans in the treatment of afflictions, the prescribing physician will ultimately determine the appropriate dose for a given human subject, and this can be expected to vary according to the age, weight, and response of the individual as well as the nature and severity of the patient's symptoms. Due to the reduced toxicity of liposome entrapped bioactive agents, dosages higher than those normally used for the agents alone may be administered. It may be desirable to initiate therapy with a dosage of about that typically used for the agent alone and then increase the dosage as deemed appropriate to the patient and the circumstances.

The sites and cells in the organism to which the agent is desired to be delivered may determine the mode of administration. For instance, delivery. to a specific external site may be most easily accomplished by topical application. Such topical application may be in the form of creams or ointments. Alternatively, administration may be effected by absorption through epithelial or mucocutaneous linings (e.g., nasal, oral, vaginal, rectal, gastrointestinal, mucosa, etc.). The liposome compositions of the present invention can be administered alone, but will generally be administered in admixture with a pharmaceutical carrier selected with regard to the intended route of administration and standard pharmaceutical practice. They may be injected parenterally, for example, intravenously, intramuscularly, or subcutaneously. For parenteral administration, they are best used in the form of a sterile aqueous solution which may contain other solutes, for example, enough salts or glucose to make the solution isotonic.

For an oral mode of administration, liposome compositions of the present invention can be used in the form of tablets, capsules, lozenges, troches, powders, syrups, elixirs, aqueous solutions and suspensions, and the like. In the case of tablets, carriers which can be used include lactose, sodium citrate, and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, certain sweetening and/or flavoring agents can be added.

Alternatively, the liposome compositions of the present invention may be used in vitro, e.g., as diagnostic agents. For example, an agent possessing a reporter group may be entrappeal in liposomes to which a targeting molecule is attached to the outermost layer. Targeting molecules include antigens and antibodies, as well as a number of other binding partners to molecules which may reside in a sample to be tested in vitro. Dyes, such as rhodamine, merocyanine, porphyrine and phthalocyanine, provide a convenient means to detect the presence or absence of binding of a liposome to a sample. Targeting molecules may be coupled to liposomes by a variety of techniques (e.g., as described in U.S. Pat. No. 5,171,578). The amount of the particular composition used will depend on the sensitivity of the liposome-coupled targeting molecule to the target components in the sample.

The following examples are offered by way of illustration and not by way of limitation.

EXAMPLES

Example 1

PREPARATION OF LIPOSOMAL VINCRISTINE

Figure 6:
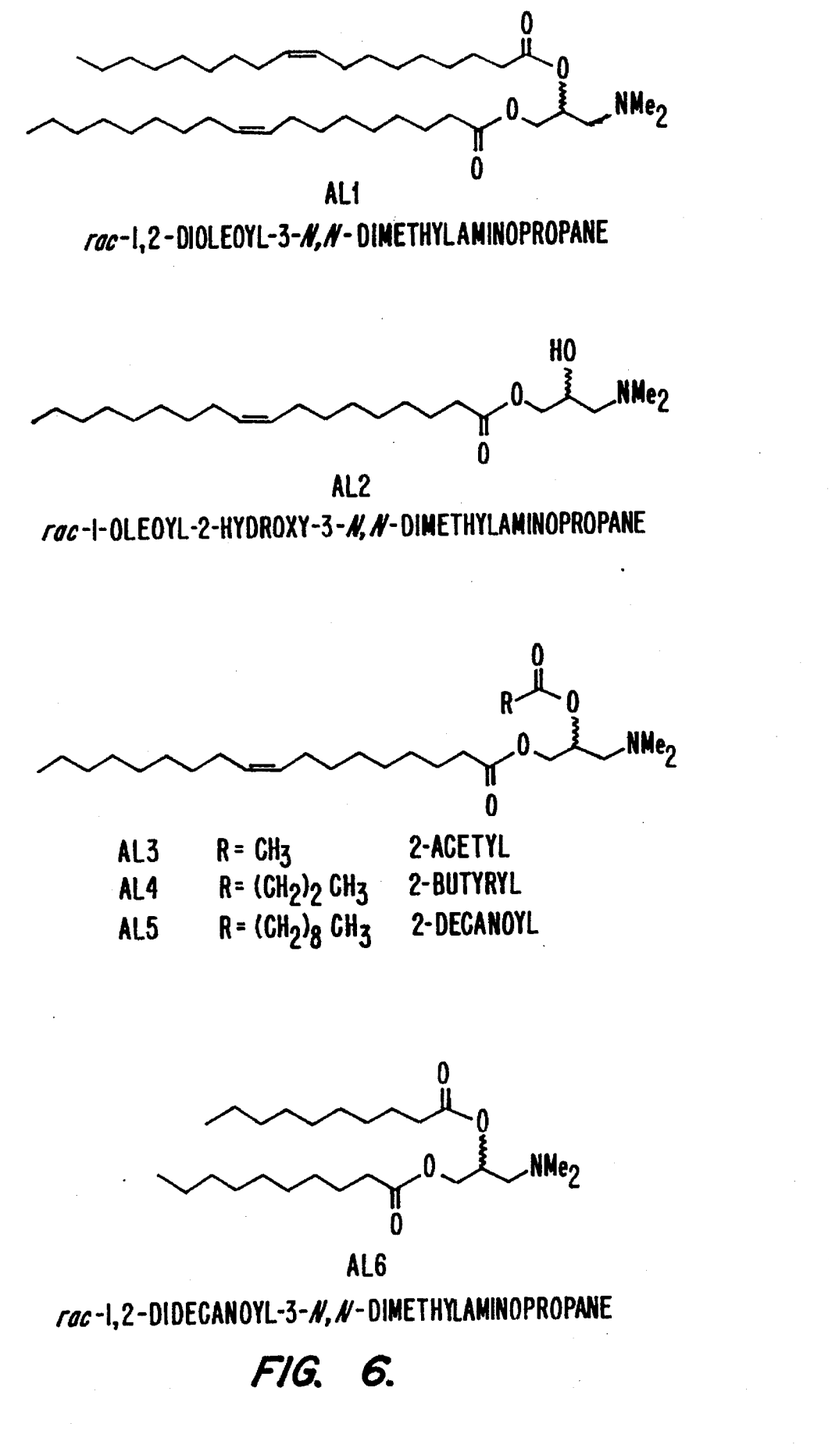
FIG. 6 depicts the chemical structures of the amino lipids designated AL-1, AL-2, AL-3, AL-4, AL-5 and AL-6.

"Oncovin" (vincristine sulfate) was obtained from the B.C. Cancer Agency (Vancouver, British Columbia, Canada). Distearoylphosphatidylcholine ("DSPC") was purchased from Avanti Polar Lipids (Alabaster, AL), and was greater than 99% pure. Monosialoganglioside $G_{M1}$, cholesterol ("chol"), and all salts were obtained from Sigma Chemical Company (St. Louis, Mo.). Cholesteryl hexadecylether ($^{14}$C), a lipid marker that is not exchanged or metabolized in vivo, was specially synthesized by Amersham (Oakville, Ontario). Amino lipids AL-1 to AL-6, as depicted in FIG. 6, were prepared as described in Example 4 below. Female BDF1 mice (6–8 weeks old) were purchased from Charles .River Laboratories.

DSPC/Chol (55:45; mol:mol), DSPC/Chol/$G_{M1}$ (45:45:10; mol:mol:mol), DSPC/Chol/Stearylamine (45:45:10), DSPC/Chol/AL-1 (45:45:10), or DSPC/Chol/Sphingosine (45:45:10) were prepared by dissolving the lipid mixtures in 95% ethanol (1 mL/100 mg lipid). The mixtures were then heated at 60° C. for 30 min. Subsequently, a preheated (60° C.) solution of 300 mM citric acid (pH 4 or pH 2) was added (3 mL buffer/100 mg total lipid) while vigorously vortex mixing. The resulting multilamellar vesicles ("MLVs") were heated at 60° C. for an additional 30 min., followed by extrusion ten times through two polycarbonate filters with 100 nm pores. The extrusion device, obtained from Lipex Biomembranes (Vancouver, British Columbia, Canada), was also maintained at 60° C. Ethanol was removed from the liposome preparation by dialyzing (Spectra/Por 2 dialysis tubing, 12,000–14,000 molecular weight cut-off against two changes (200 mL dialysis buffer per 1 mL of sample) of 300 mM citric acid (pH 4 or 2) over a 24 h period. It has been determined that greater than 99.9% of the ethanol is removed using this procedure.

Vincristine was entrapped in the liposomes using a ΔpH loading procedure based upon that described by Mayer et al. (*Cancer Res.* 50:575–579, 1990), but significantly modified by the use of a low pH in the solution entrapped (e.g., pH 2 as described above). Vesicles (25 mg/mL) were added to vincristine ("Oncovin" solution, 1 mg vincristine/mL) to achieve a drug-to-lipid ratio of 0.1:1. The exterior pH of the liposome/vincristine mixture was raised to pH 7.0–7.2 with 0.5M Na$^2$HPO$_4$ and immediately heated to 60° C. for 10 min. Vincristine entrapment was determined by column chromatography techniques (Mayer et al., *Biochem.* 27:2053–2060, 1988) using $A_{297}$ (in ethanol/H$_2$O, 8/2) and $A_{815}$ spectroscopic assays for quantitation of vincristine and lipid, respectively, or using liquid scintillation counting of $^1$4C-cholesteryl hexadecylether and $^3$H-vincristine.

Example 2

PLASMA CLEARANCE AND IN VIVO DRUG RELEASE

Plasma clearance studies were performed by injecting 20 mg lipid/kg of drug loaded or empty liposomes (prepared according to Example 1 ) via a lateral tail vein to female BDF1 mice (18–22 g). The vincristine dose was therefore typically 2 mg/kg. Previous studies have shown that this dose of vincristine, when entrapped in liposomes, exhibits measurable levels of antitumor activity in L 12 10 and P388 ascites tumor models (Mayer et al., *Cancer Res.* 50:575, 1990). Four mice were used per time point. The mice were anaesthetized at the indicated time points (i.p. mixture of ketamine 160 mg/kg and xylazine 20 mg/kg). Blood was collected via cardiac puncture and placed into EDTA coated microtainer tubes (Becton Dickinson). The samples were then centrifuged (500 x g for 10 min) to pellet the blood cells and obtain plasma samples. Liposomal lipid and/or vincristine were then assayed using scintillation counting.

Biodistribution studies were performed on the same mice used for plasma clearance studies. Following heart puncture, animals were euthanized by cervical dislocation, and selected tissues were removed from each animal and weighed. Saline was added to each organ to achieve a 10% (w/v) homogenate using a Polytron homogenizer (Brinkmann Instruments, Rexdale, Ont.). Tissue homogenates (500 µL) were digested with 500 µL of "Solvable" (DuPont Canada, Inc., Mississauga, Ont.) for 3 h at 50° C. Subsequently, the samples were cooled to room temperature before decolorizing with 200 µL of 30% hydrogen peroxide. Samples were then counted using Picofluor (Packard) scintillation cocktail. The statistical significance of both the plasma clearance and biodistribution results were determined employing the student's t-test.

The influence of $G_{M1}$ incorporation and entrapped vincristine on the circulation time of 100 nm DSPC/Chol liposomes is shown in FIG. 1A. Two important conclusions can be derived from this data. First, the circulation lifetime of liposomes with entrapped vincristine is greater than control, drug-free, liposomes. This effect cannot be achieved with free drug pre-treatment. Second, incorporation of 10 mol % $G_{M1}$ in 100 nm DSPC/Chol liposomal vincristine results in a further increase in carrier circulation lifetime. Plasma liposomal lipid levels are increased approximately 2.5-fold 24 h after i.v. administration when $G_{M1}$ is incorporated into DSPC/Chol liposomal vincristine. Liposomal lipid accumulation in liver and spleen (FIG. 1B and C) is reduced significantly when $G_{M1}$/DSPC/Chol liposomes are used to encapsulate vincristine.

Figure 2A:
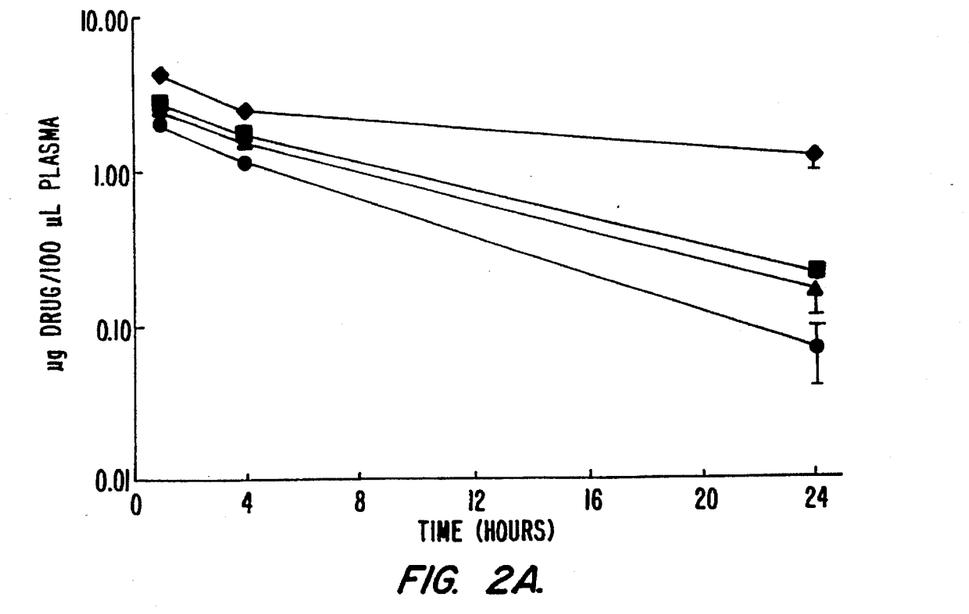
FIGS. 2A–B graphically illustrate the plasma clearance of vincristine (panel A) and associated drug-to-lipid ratios (panel B) as determined following i.v. administration in mice of liposomal vincristine prepared using: DSPC/Chol pH 4 (●), $G_{M1}$/DSPC/Chol pH 4 (■), DSPC/Chol pH 2 (▲) and $G_{M1}$/DSPC/Chol pH 2 (♦) liposomes. Vincristine was encapsulated at a drug-to-lipid ratio of 0.1:1 (wt:wt) and was measured using $^3H$ vincristine as a tracer. Error bars represent standard deviations from at least four mice.
Figure 2B:
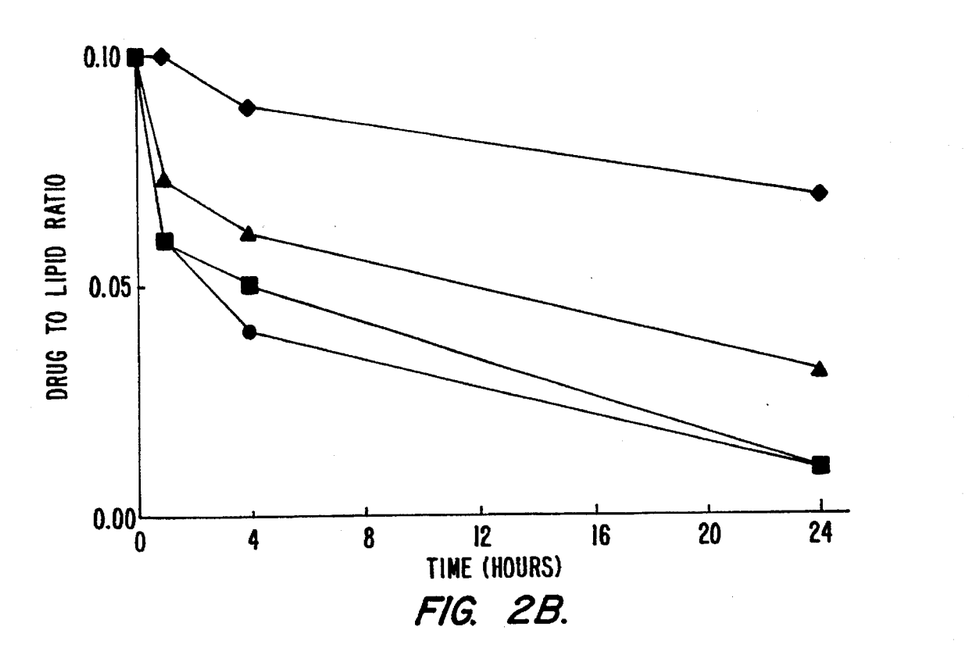

The influence of $G_{M1}$ incorporation on circulating vincristine levels over 24 h after i.v. administration is shown in FIG. 2. As expected on the basis of data in FIG. 1, incorporation of $G_{M1}$ into liposomes used to encapsulate vincristine resulted in approximately a 3-fold increase in the level of drug achieved in the plasma at 24 h (FIG. 2A). The circulating drug-to-lipid ratio for these systems are shown in FIG. 2B, which shows that drug release from liposomes in the plasma compartment is not influenced by incorporation of $G_{M1}$. For these liposomal vincristine formulations, where drug was encapsulated using the pH gradient loading procedure in liposomes prepared in 300 mM citrate buffer at pH 4, greater than 90% of the encapsulated drug had been released from circulating liposomes over the 24 h time course.

Retention of vincristine entrapped in 100 nm DSPC/Chol liposomes in response to a transmembrane pH gradient can be improved by decreasing the pH of the encapsulated citrated buffer from 4 to 2. As shown in FIG. 2A, decreasing the interior pH from 4 to 2 results in a 2.5 fold increase in the circulating vincristine levels achieved at 24 h post i.v. injection. The change in intravesicular pH did not influence the clearance of injected liposomes. Therefore, the increased drug levels occur as a result of increased drug retention. At every time point studied, higher drug-to-lipid ratios were observed for vincristine encapsulated in liposomes prepared at pH 2 (FIG. 2B).

Incorporation of $G_{M1}$ in combination with the use of the pH 2 entrapped citrate buffer resulted in an unexpected improvement in vincristine circulation lifetime. Plasma vincristine levels were approximately 7.5-fold and 20-fold higher at 24 h than could be achieved with comparable systems prepared in the absence of $G_{M1}$ using the pH 2 and pH 4 buffer, respectively. As shown in FIG. 2B, $G_{M1}$/DSPC/Chol liposomes prepared at pH 2 exhibited less than a 20% decrease in circulating drug-to-lipid ratio over 24 h.

Figure 3A:
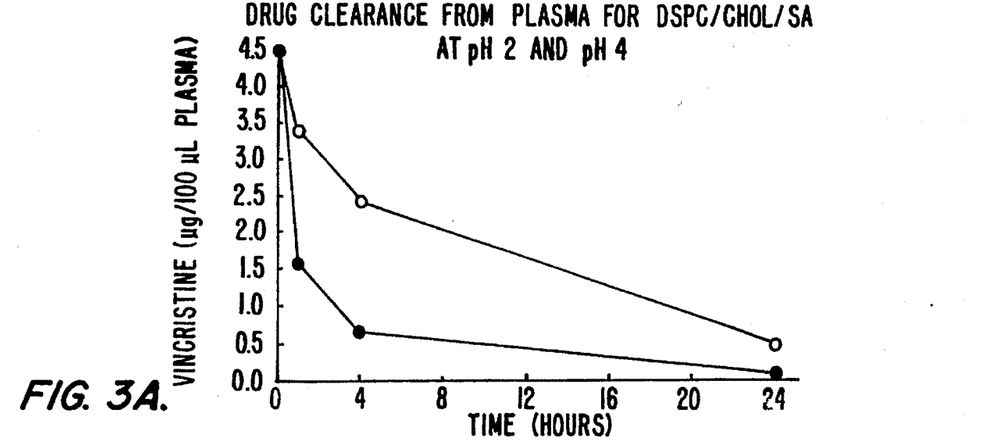
FIGS. 3A–C graphically illustrate the drug clearance (panel A), lipid clearance (panel B) and drug-to-lipid (panel C) ratios for DSPC/Chol/Stearylamine (SA) when injected into BDF1 mice at a vincristine dose of 2 mg/kg and a lipid dose of 20 mg/kg: DSPC/Chol/SA prepared at pH 2 (O), and DSPC/Chol/SA prepared at pH 4 (●).
Figure 3B:
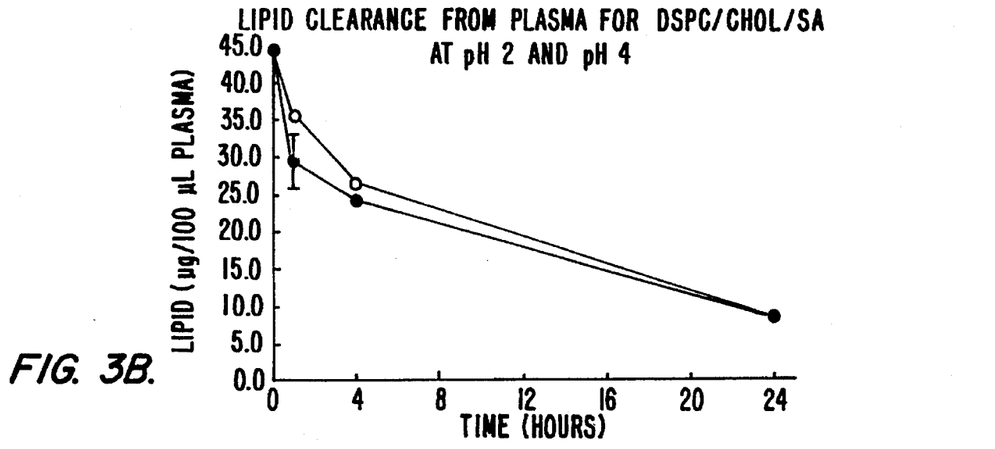
Figure 3C:
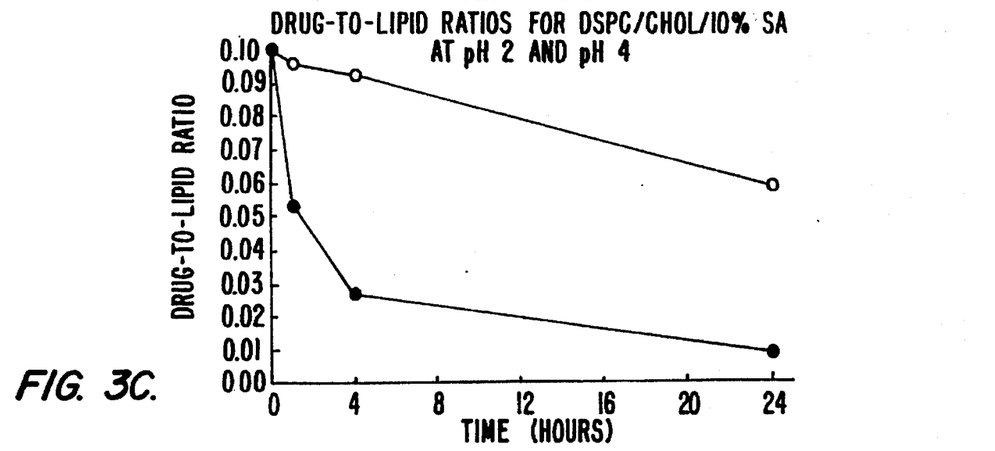
Figure 4A:
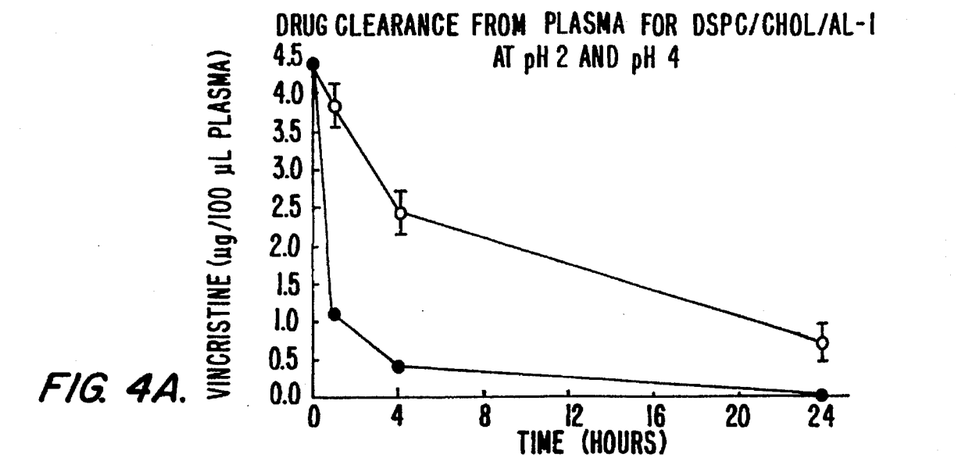
FIGS. 4A–C graphically illustrate the drug clearance (panel A), lipid clearance (panel B), and drug-to-lipid (panel C) ratios for DSPC/Chol/Aminolipid-1 (AL-1) when injected into BDF 1 mice at a vincristine dose of 2 mg/kg and a lipid dose of 20 mg/kg: DSPC/Chol/AL-1 prepared at pH 2 (O), and DSPC/Chol/AL-1 prepared at pH 4 (●).
Figure 4B:
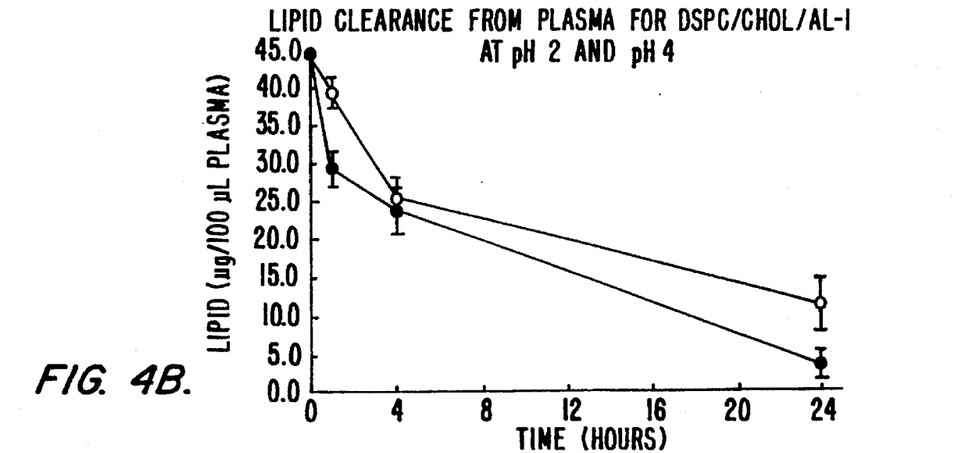
Figure 4C:
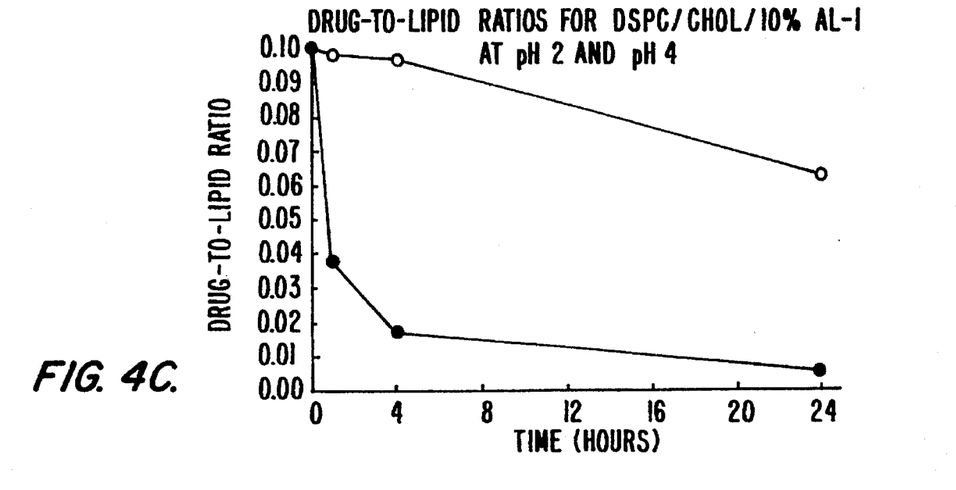
Figure 5A:
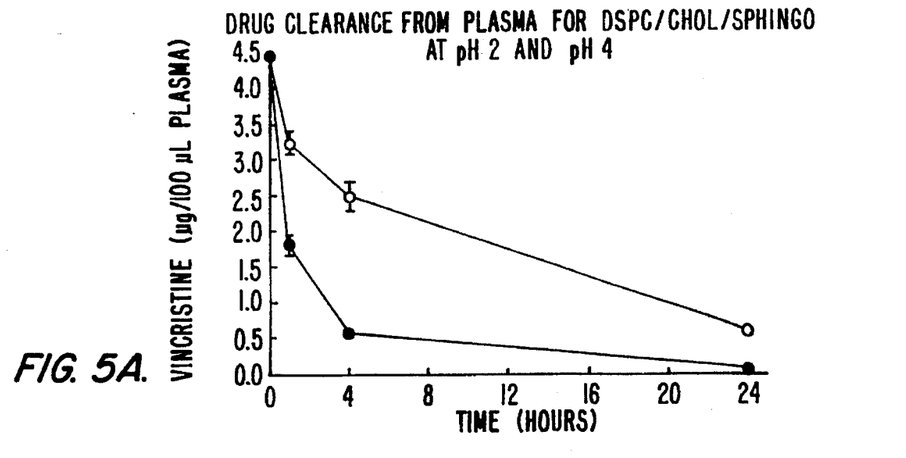
FIGS. 5A–C graphically illustrate the drug clearance (panel A), lipid clearance (panel B) and drug-to-lipid (panel C) ratios for DSPC/Chol/Sphingosine (sphingo) when injected into BDF1 mice at a vincristine dose of 2 mg/kg and a lipid dose of 20 mg/kg: DSPC/Chol/sphingo prepared at pH 2 (O), and DSPC/Chol/sphingo prepared at pH 4 (●).
Figure 5B:
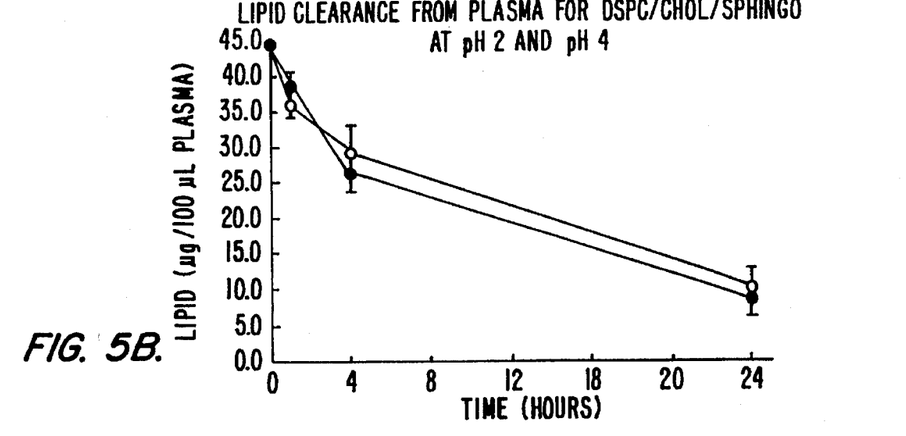
Figure 5C:
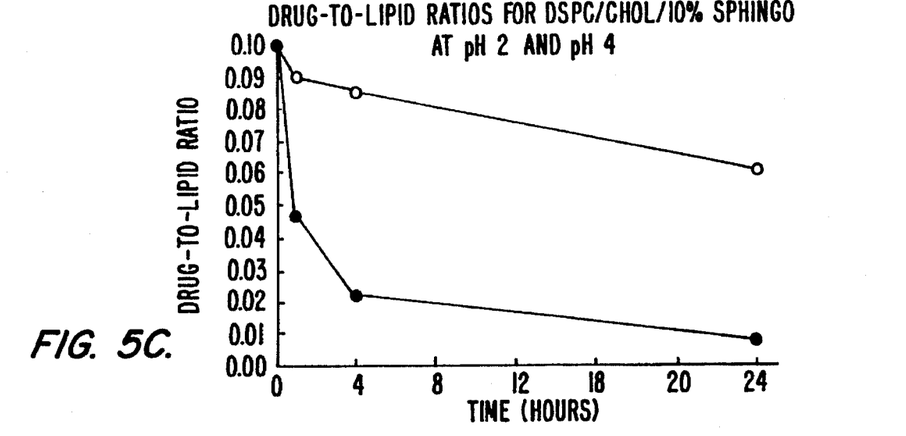

The use of amine-containing lipids to promote retention of the anti-cancer agent vincristine is illustrated in FIGS. 3-5. Selected amine lipids were incorporated at the level of 5 mol % in liposomes composed of DSPC/Chol. Large unilamellar liposomes were prepared as described in Example 1 such that the liposomes entrapped 300 mM citrate buffer at pH 4 (filled circles) or pH 2 (open circles) and exhibited a mean particle size of less than 200 nm. Three examples are provided including liposomes that contain stearylamine (FIG. 3), AL-1 (rac-1,2-dioleoyl-3-N,N-dimethylaminopropane, FIG. 4) and sphingosine (FIG. 5). Drug retention characteristics were assessed in vivo following i.v. administration of the liposomal vincristine preparation in female BDF1 mice at a drug dose of 2 mg/kg (lipid dose of 20 mg/kg). At the indicated time points (1, 4 and 24 h), blood was collected from the mice (four mice per time point) via cardiac puncture. The blood was immediately placed into EDTA coated microtainers. Subsequently, plasma was prepared by centrifugation of the collected blood. Liposomal lipid and vincristine in the plasma were measured using radiolabeled markers ($^3$[H]-Vincristine and $^{14}$[C]-Cholesterylhexadecylether). The resulting data demonstrates that significantly improved vincristine retention is achieved when amine-containing lipids are incorporated in liposomes with pH 2 citrate buffer. In contrast to the same formulations prepared using pH 4 buffer, there is typically a 7–8 fold increase in the drug-to-lipid ratio observed in plasma collected from animals 24 h after drug administration (Panel C, FIGS. 3–5).

Example 3

ANTITUMOR ACTIVITY OF LIPOSOMAL VINCRISTINE

The antitumor effects of liposomal vincristine were monitored using the P388 lymphocytic leukemia model. BDF1 mice (5 per group) were injected i.p. with $1 \times 10^6$ P388 cells. The indicated doses of saline or liposomal vincristine were administered (i.v.) 24 h after tumor inoculation. Animal weights and mortality were monitored daily. Mean and median survival times as well as the statistical significance of the results were determined using the Mann-Whitney-Wilcoxon procedure.

Tumor efficacy studies were conducted to determine whether the improved vincristine circulation lifetime achieved through the use of $G_{M1}$ and reduced internal pH improves the therapeutic activity of the entrapped drug. Murine P388 antitumor activity of the DSPC/Chol/$G_{M1}$ pH 2 liposomal vincristine preparation was compared to free drug and DSPC/Chol pH 4 liposomal vincristine (Table I below).

The two liposomal preparations exhibited a 12-fold difference in circulation half-life as estimated from the data in FIG. 2A. The liposomal formulations were significantly more efficacious in the P388 tumor model when compared to free drug. The liposomal formulation which combined the use of $G_{M1}$ and the reduced internal pH exhibited remarkable activity in this model. This formulation, when administered at 2, 3 and 4 mg/kg, consistently produced long-term survival rates in excess of 50%. Similarly, another liposomal formulation which combined the use of sphingosine and reduced internal pH also consistently produced long-term survival rates. No long-term survivors (>70 days) were obtained with either free drug or the DSPC/Chol pH 4 liposomal vincristine formulations. Drug induced weight loss data (% decrease in weight on day 7) shown in Table I also suggest a decrease in drug toxicity for the $G_{M1}$/DSPC/Chol pH 2 liposomes compared to DSPC/Chol pH 4 liposomes.

TABLE I

| | P388 Antitumor Activity of Free and Liposomal Vincristine in BDFI Mice | | | | | | |
|---|---|---|---|---|---|---|---|
| Sample | Drug Dose (mg/kg) | Lipid Dose (mg/kg) | % wt change on day 7 | 60-day Survival | Median Survival (days) | % ILS[a] | L/F[b] |
| Saline control | | | +9.8 | 0/10 | 10.0 | | |
| Free Vincristine | 1.0 | 10 | +1.9 | 0/5 | 14.0 | 40 | |
| | 2.0 | 20 | +0.5 | 0/5 | 15.0 | 50 | |

TABLE I-continued

P388 Antitumor Activity of Free and Liposomal Vincristine in BDFI Mice

| Sample | Drug Dose (mg/kg) | Lipid Dose (mg/kg) | % wt change on day 7 | 60-day Survival | Median Survival (days) | % ILS[a] | L/F[b] |
|---|---|---|---|---|---|---|---|
| | 3.0 | 30 | −13.4 | 0/5 | 16.0 | 60 | |
| DSPC/ | 1.0 | 10 | +2.8 | 0/5 | 22.0 | 120 | 1.57 |
| Cholesterol | 2.0 | 20 | −2.1 | 0/10 | 27.0 | 170 | 1.80 |
| pH 4.0 | 3.0 | 30 | −12.0 | 0/10 | 31.0 | 210 | 1.94 |
| Lipovinc | 4.0 | 40 | −24.9 | 0/10 | 32.0 | 220 | — |
| DSPC/ | 1.0 | 10 | +3.3 | 1/5 | 20.0 | 100 | 1.43 |
| Chol/$G_{M1}$ | 2.0 | 20 | +0.2 | 8/10 | >70.0 | ND[c] | ND |
| pH 2.0 | 3.0 | 30 | −10.9 | 10/10 | >70.0 | ND | ND |
| Lipovinc | 4.0 | 40 | −14.4 | 10/10 | >70.0 | ND | — |
| DSPC/ | 2.0 | 20 | +1.7 | 1/5 | 36.0 | 260 | 2.40 |
| Chol/ | 3.0 | 30 | −7.0 | 3/5 | >60.0 | ND | ND |
| Sphingosine pH 2.0 Lipovinc | 4.0 | 40 | −18.5 | 3/5 | >60.0 | ND | ND |

[a]Percentage of ILS (increase in life span) values were determined from median survival time comparing treated and saline control groups. If greater than 50% of the animals survived for greater than 70 days, median survival times and % ILS were not calculated.
[b]L/F (liposomal/free) values were calculated by dividing the median survival time for the liposomal vincristine group by the median survival time for the equivalent dosage of free drug.
[c]N.D. - not determined.

Example 4

PREPARATION OF AMINO LIPIDS AL-1 TO AL-6

A. Synthesis of ±1,2-dioleoyl-3-N,N-dimethylamino-propane (AL-1). This compound was prepared by the method of Leventis et al. (*Biochim. Biophys. Acta* 1029:124–132, 1990). Three ml (35 mmol) of oxalyl chloride was added to 1.0 g (3.5 mmol) oleic acid dissolved in 10 ml benzene and stirred at room temperature for 1 h. After removal of solvent and excess oxalyl chloride under vacuum, the acid chloride was dissolved in 5 ml diethyl ether, and a further 5 ml of ether containing 0.20 g (1.7 mmol) of 3-N,N-dimethylamino-1,2-propanediol and 0.15 g pyridine was added. The resulting mixture was stirred at room temperature for 30 minutes before quenching with 1 ml methanol and removing solvents under vacuum. The crude product was dissolved in 50 ml hexane and washed with 2×25 ml 0.1M potassium hydroxide in methanol/water (1:1) followed by 25 ml 0.1M aqueous sodium chloride. Drying over anhydrous sodium sulphate and removal of hexane under vacuum gave a slightly yellow oil. Column chromatography on silica gel (70–230 mesh), eluting with ethyl acetate, gave 0.92 g (84%) of pure product (TLC, $R_f$=0.5). The structure of the product was confirmed by 200 MHz $^1$H-NMR. An analogous procedure with decanoyl chloride was used to prepare ±-1,2-didecanoyl-1-N,N-dimethylaminopropane (AL-6).

B. Synthesis of ±-1-oleoyl-2-hydroxy-3-N,N-dimethylaminopropane (AL-2) and asymmetric ±-1,2-diacyl-3-N,N-dimethylaminopropanes (AL3-ALS). Oleoyl chloride (3.5 mmol), prepared as above, was dissolved in 5 ml THF and added to a five-fold excess of 3-N,N-dimethylamino-1,2-propanediol (2.0 g, 17 mmol) and 0.15 g pyridine in 25 ml THF at 0° C. Crude 1-monooleoyl-2-hydroxy-3-N,N-dimethylaminopropane (AL-2) was isolated as above and purified by column chromatography on silica gel using ethyl acetate/methanol (3:1) as eluant ($R_f$ 0.4). Subsequent acylation with one equivalent of acetyl chloride, butyryl chloride, or decanoyl chloride with reaction conditions, extraction procedures, and purification as described above produced AL-3, AL-4, and AL-5, respectively.

From the foregoing, it will be evident that, although specific embodiments of the invention have been described herein for purposes of illustration, various modifications may be made without deviating from the spirit and scope of the invention.

We claim:

1. A composition comprising liposomes having encapsulated therein both a bioactive agent and a buffered solution having a pH of 2 to 3, said liposomes containing a sugar-modified lipid which is a ganglioside and cerebroside in an amount of about 10 mol percent.

2. A composition according to claim 1 wherein said solution is pH 2.

3. A composition according to claim 1 wherein said sugar-modified lipid is a ganglioside selected from the group consisting of $G_{M1}$, $G_{M2}$ and $G_{M3}$.

4. A composition according to claim 3 wherein said bioactive agent is an anticancer agent.

5. A composition according to claim 3 wherein said solution is buffered with citrate, maleate or glutamate.

6. A composition according to claim 3, further comprising a pharmaceutically acceptable carrier or diluent.

7. A composition comprising liposomes produced by (a) hydrating a lipid film in a buffered first solution having a pH of 2 to 3 to yield liposomes, said lipid film containing a sugar-modified lipid which is a ganglioside and cerebroside in an amount of about 10 mol percent;

(b) contacting said liposomes with a second solution, said second solution containing a bioactive agent to provide a liposomal bioactive agent mixture;

(c) increasing the pH of said mixture in step (b) to a pH not above the $pK_a$ of the bioactive agent to provide a liposomal mixture having a pH differential; and (d) incubating said mixture having a pH differential under conditions and for a time sufficient to promote entrapping of said bioactive agent by said liposomes, thereby producing liposomes that encapsulate a bioactive agent and that contain a sugar-modified lipid ganglioside and cerebroside in an amount of about 10 mol percent.

8. A composition according to claim 7 in combination with a pharmaceutically acceptable carrier or diluent.

9. A method for treating cancer in a warm-blooded animal, comprising administering a therapeutically effective amount of a composition according to claim 4 wherein said bioactive agent is an anticancer agent.

10. A method for treating cancer in a warm-blooded animal, comprising administering a therapeutically effective amount of a composition according to claim 8 wherein said bioactive agent is an anticancer agent.

* * * * *